United States Patent [19]

Takai et al.

[11] 4,344,948
[45] Aug. 17, 1982

[54] PIPERIDINE DERIVATIVES AND PHARMACEUTICAL COMPOSITIONS CONTAINING SAME

[75] Inventors: Haruki Takai, Kawasaki; Masayuki Teranishi; Nobuhiro Nakamizo, both of Machida; Yutaka Kasuya, Kawasaki, all of Japan; Kazuhiro Kubo, Berchem, Belgium

[73] Assignee: Kyowa Hakko Kogyo Co., Ltd., Tokyo, Japan

[21] Appl. No.: 209,284

[22] Filed: Nov. 21, 1980

[30] Foreign Application Priority Data

Nov. 21, 1979 [JP] Japan .................................. 54/150056

[51] Int. Cl.³ .................. C07D 401/04; A61K 31/505
[52] U.S. Cl. .................... 424/251; 542/423; 544/250; 544/286; 546/199
[58] Field of Search ............................. 544/250, 286; 260/244.4; 424/251, 267; 260/239.3 B

[56] References Cited

U.S. PATENT DOCUMENTS 3,454,574  7/1969  Keck et al. ......................... 544/286
3,819,627  6/1974  Ott ..................................... 544/286
3,829,420  8/1974  Inaba et al. ........................ 544/286

*Primary Examiner*—Donald G. Daus
*Assistant Examiner*—James H. Turnipseed
*Attorney, Agent, or Firm*—Craig and Antonelli

[57] ABSTRACT

A new piperidine derivative represented by the formula:

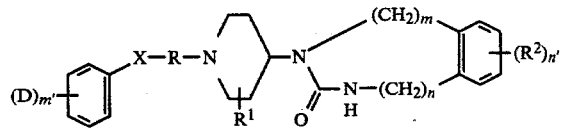

wherein X is oxygen, sulfur, carbonyl, hydroxymethylene or methylene; R is straight-chain alkylene having 1–4 carbon atoms with or without lower alkyl substituent(s); m and n are 0 or 1, and are different from each other (i.e., both m and n are not 0 or 1); and $(D)_{m'}$, $R^1$ and $(R^2)_{n'}$ are usually used as substituents, has a hypotensive activity.

6 Claims, No Drawings

PIPERIDINE DERIVATIVES AND PHARMACEUTICAL COMPOSITIONS CONTAINING SAME

The present invention relates to novel piperidine derivatives, acid addition salts thereof and pharmaceutical compositions containing the same.

More specifically, the present invention relates to novel piperidine derivatives represented by the general formula [I]:

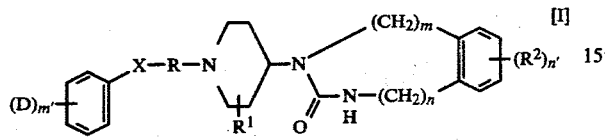

[wherein m' is 0 or an integer of 1–5 representing the number of D groups substituted on the benzene ring; D is hydroxy, halogen, lower alkyl, lower alkoxy, lower alkenyloxy, lower alkynyloxy, lower alkylthio, carboxy, lower alkoxycarbonyl, nitro, amino, lower alkylamino, lower alkanoylamino, sulfamoyl, mono- or di-lower alkylaminosulfonyl, lower alkylsulfonyl, carbamoyl, cyano or trifluoromethyl, and when m' is 2 or more, each D is the same group or each D is a different group or two D groups may combine to form lower alkylenedioxy; X is oxygen, sulfur, carbonyl, hydroxy-methylene or methylene; R is straight-chain alkylene having 1-4 carbon atoms with or without lower alkyl substituent(s); $R^1$ is hydrogen or lower alkyl; m and n are 0 or 1, and when one of m and n is 0, the other is 1, n' is 0 or an integer of 1-4 representing the number of $R^2$ group on the benzene ring; and $R^2$ is hydroxy, lower alkoxy, halogen, trifluoromethyl, trifluoromethoxy, trifluoromethylthio, nitro or amino, and when n' is 2 or more, each $R^2$ is the same group or each $R^2$ is a different group or two $R^2$ groups may combine to form a lower alkylenedioxy] (hereinafter often referred to as Compound [I]) and pharmacologically acceptable acid addition salts thereof, and pharmaceutical compositions comprising pharmaceutically acceptable carrier(s) and a compound represented by the general formula [I] or a pharmacologically acceptable acid addition salt thereof.

Heretofore, the following compounds, each having a piperidine ring, are commercially available as tranquilizers:

benperidol

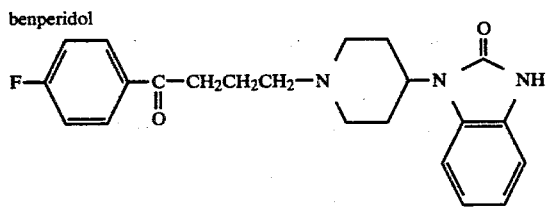

droperidol

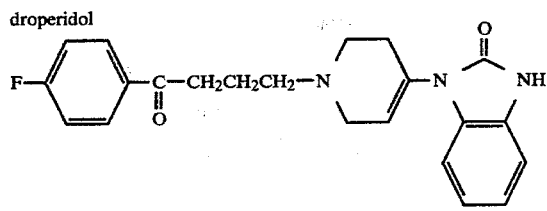

pimozide

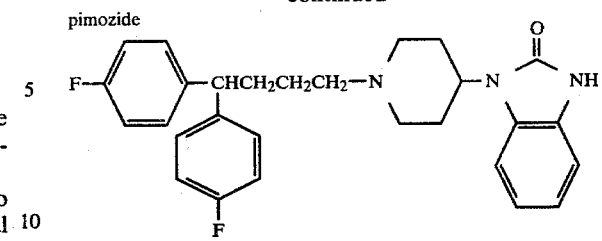

Further, an application for patent relating to compounds which have a hypotensive activity and are substantially represented by the following general formula:

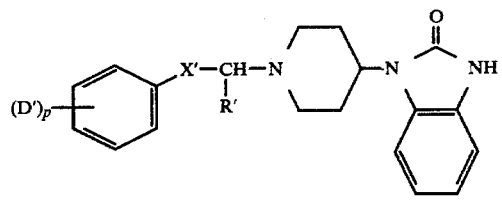

(wherein p is 0 or an integer of 1-3; D' is methoxy or two D' groups may combine to form methylenedioxy; X' is carbonyl, hydroxymethylene or methylene; and R' is hydrogen or methyl) is pending (U.S. patent application Ser. No. 191,339, filed on Jan. 31, 1980).

Compounds having excellent pharmacological activities are in great demand. In order to obtain such compounds, studies have been made on piperidine derivatives and as a result, it has been found that novel piperidine derivatives represented by the general formula [I] have a hypotensive activity. Further, it has been found that some compounds represented by the formula for Compound [I] above have an antiulcer activity or an activity against blood platelet aggregation.

The present invention is explained in more detail below.

The term "halogen" in the definition of D and $R^2$ in Compound [I] includes chlorine, bromine, etc.; "lower" in the definition of the various groups in Compound [I] means having 1-5 carbon atoms, especially 1-3.

Compound [I] includes all of the optical isomers.

Examples of pharmacologically acceptable acid addition salts of Compound [I] are inorganic acid addition salts such as hydrochloride, hydrobromide, hydroiodide, nitrate, sulfate and phosphate, and organic acid addition salts such as acetate, benzoate, maleate, fumarate, succinate, tartrate, citrate, oxalate, glyoxylate, aspartate, methanesulfonate, ethanesulfonate, propanesulfonate, methanedisulfonate, α,β-ethanedisulfonate and benzenesulfonate.

Especially preferable compounds within the formula representing Compound [I] are represented by the general formula [I']:

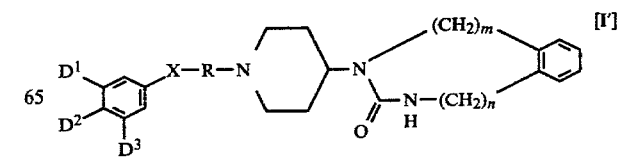

(wherein $D^1$, $D^2$ and $D^3$ each are the same group or each are a different group, and $D^1$, $D^2$ and $D^3$ are hydrogen or have the same definition as that of above-mentioned D group in Formula [I]; and X, R, m and n have the same meaning or definition as defined above in Formula [I].

Examples of Compound [I] are tabulated in the following Table 1. Table 2 shows structures and Tables 3-1, 2 and 3 show properties of the present compounds.

TABLE 1

| Compound No. | Compound |
|---|---|
| 1 | 1-(3,4-dimethoxybenzoylmethyl)-4-[3,4-dihydro-2(1H)-quinazolinon -3-yl]piperidine |
| 2 | 1-(3,4-methylenedioxybenzoylmethyl)-4-[3,4-dihydro-2(1H)-quinazolinon -3-yl]piperidine |
| 3 | 1-[2-(3,4-dimethoxyphenyl)-2-hydroxyethyl]-4-[3,4-dihydro-2(1H)-quinazolinon -3-yl]piperidine |
| 4 | 1-[2-(3,4-methylenedioxyphenyl)-2-hydroxyethyl]-4-[3,4-dihydro-2(1H)-quinazolinon -3-yl]piperidine |
| 5 | 1-[1-(3,4-dimethoxybenzoyl)ethyl]-4-[3,4-dihydro-2-(1H)-quinazolinon-3-yl]piperidine |
| 6 | 1-[3-(3,4-dimethoxyphenyl)-3-hydroxypropyl-2]-4-[3,4-dihydro-2(1H)-quinazolinon -3-yl]piperidine |
| 7 | 1-[2-(3,4,5-trimethoxyphenyl)-2-hydroxyehtyl]-4-[3,4-dihydro-2(1H)-quinazolinon -3-yl]piperidine |
| 8 | 1-(3,4-dimethoxybenzoylmethyl)-4-[3,4-dihydro-2(1H)-quinazolinon -1-yl]piperidine |
| 9 | 1-(3,4-methlenedioxybenzoylmethyl)-4-[3,4-dihydro-2(1H)-quinazolinon -1-yl]piperidine |
| 10 | 1-[2-(3,4-dimethoxyphenyl)-2-hydroxyehtyl]-4-[3,4-dihydro-2(1H)-quinazolinon -1-yl]piperidine |
| 11 | 1-[2-(3,4-methylenedioxyphenyl)-2-hydroxyethyl]-4-[3,4-dihydro-2(1H)-quinazolinon -1-yl]piperidine |
| 12 | 1-[1-(3,4-dimethoxybenzoyl)ehtyl]-4-[3,4-dihydro-2(1H)-quinazolinon -1-yl]piperidine |
| 13 | 1-[3-(3,4-dimethoxyphenyl)-3-hydroxypropyl-2]-4-[3,4-dihydro-2(1H)-quinazolinon -1-yl]piperidine |
| 14 | 1-benzoylmethyl-4-[3,4-dihydro-2(1H)-quinazolinon-3-yl]piperidine |
| 15 | 1-(3-chlorobenzoylmethyl)-4-[3,4-dihydro-2(1H)-quinazolinon-3-yl]piperidine |
| 16 | 1-(4-chlorobenzoylmethyl)-4-[3,4-dihydro-2(1H)-quinazolinon -3-yl]piperidine |
| 17 | 1-(4-methoxybenzoylmethyl)-4-[3,4-dihydro-2(1H)-quinazolinon -3-yl]piperidine |
| 18 | 1-(2-phenyl-2-hydroxyethyl)-4-[3,4-dihydro-2(1H)-quinazolinon -3-yl]piperidine |
| 19 | 1-[2-(3-chlorophenyl)-2-hydroxyethyl]-4-[3,4-dihydro-2(1H)-quinazolinon -3-yl]piperidine |
| 20 | 1-[2-(4-chlorophenyl)-2-hydroxyethyl]-4-[3,4-dihydro-2(1H)-quinazolinon -3-yl]piperidine |
| 21 | 1-[2-(4-methoxyphenyl)2-hydroxyethyl]-4-[3,4-dihydro-2(1H)-quinazolinon -3-yl]piperidine |
| 22 | 1-[2-(3,4-dichlorophenyl)-2-hydroxyethyl]-4-[3,4-dihydro-2(1H)-quinazolinon -3-yl]piperidine |

TABLE 2

Structure (with substituents $D^1$, $D^2$, $D^3$, X, R, m, n on the general formula shown)

| Compound No. | $D^1$ | $D^2$ | $D^3$ | X | R | m | n |
|---|---|---|---|---|---|---|---|
| 1 | OMe | OMe | H | —C(=O)— | —CH₂— | 1 | 0 |
| 2 | O—CH₂—O (3,4-methylenedioxy) | | H | —C(=O)— | —CH₂— | 1 | 0 |
| 3 | OMe | OMe | H | —CH(OH)— | —CH₂— | 1 | 0 |
| 4 | O—CH₂—O | | H | —CH(OH)— | —CH₂— | 1 | 0 |
| 5 | OMe | OMe | H | —C(=O)— | —CH(CH₃)— | 1 | 0 |
| 6 | OMe | OMe | H | —CH(OH)— | —CH(CH₃)— | 1 | 0 |
| 7 | OMe | OMe | OMe | —CH(OH)— | —CH₂— | 1 | 0 |
| 8 | OMe | OMe | H | —C(=O)— | —CH₂— | 0 | 1 |
| 9 | O—CH₂—O | | H | —C(=O)— | —CH₂— | 0 | 1 |
| 10 | OMe | OMe | H | —CH(OH)— | —CH₂— | 0 | 1 |
| 11 | O—CH₂—O | | H | —CH(OH)— | —CH₂— | 0 | 1 |
| 12 | OMe | OMe | H | —C(=O)— | —CH(CH₃)— | 0 | 1 |
| 13 | OMe | OMe | H | —CH(OH)— | —CH(CH₃)— | 0 | 1 |
| 14 | H | H | H | —C(=O)— | —CH₂— | 1 | 0 |
| 15 | Cl | H | H | —C(=O)— | —CH₂— | 1 | 0 |
| 16 | H | Cl | H | —C(=O)— | —CH₂— | 1 | 0 |
| 17 | H | OMe | H | —C(=O)— | —CH₂— | 1 | 0 |
| 18 | H | H | H | —CH(OH)— | —CH₂— | 1 | 0 |
| 19 | Cl | H | H | —CH(OH)— | —CH₂— | 1 | 0 |

TABLE 2-continued

Structure:

D¹–, D²–, D³– substituted on benzene ring with X–R–N–piperidine–N(C=O)NH–(CH$_2$)$_n$–phenyl, where piperidine has –(CH$_2$)$_m$– linker.

| Compound No. | D¹ | D² | D³ | X | R | m | n |
|---|---|---|---|---|---|---|---|
| 20 | H | Cl | H | —CH(OH)— | —CH$_2$— | 1 | 0 |
| 21 | H | OMe | H | —CH(OH)— | —CH$_2$— | 1 | 0 |
| 22 | Cl | Cl | H | —CH(OH)— | —CH$_2$— | 1 | 0 |

TABLE 3

Properties (Melting point, IR, NMR and Elementary analysis)

(1) The term "form" means the state of a compound subjected to the determination of properties.
Blank: free base
H$_2$O: water of crystallization
EtOH: ethanol of crystallization (2) The values in the column of infrared absorption spectrum (IR) show characteristic maximum absorption of the compounds measured in KBr tablet.

(3) The values in the table of nuclear magnetic resonance spectrum (NMR) are δ values based on TMS in CDCl$_3$ (Compound Nos. 1–6, 8–14, 17 and 18) or d$_6$-dimethylsulfoxide (Compound Nos. 7, 15, 16 and 19–22).

(4) Elementary analysis
A: Calculated
F: Found

TABLE 3-1

| Compound No. | Form | m.p. (°C.) | IR (cm$^{-1}$) |
|---|---|---|---|
| 1 | | 161–163.5 | 1680, 1665 |
| 2 | | 187–189.5 | 1685, 1668 |
| 3 | | 196.5–197.1 | 1670 |
| 4 | | 229.5–231.5 | 1668 |
| 5 | | 173.0–174.5 | 1680–1660 |
| 6 | ½ H$_2$O | 220.0–223.0 | 1665 |
| 7 | | 236.0–238.5 | 1660 |
| 8 | ½ EtOH | 146.0–148.0 | 1685–1670 |
| 9 | ½ EtOH | 171.0–173.0 | 1660–1690 |
| 10 | | 173.5–175.0 | 1668 |
| 11 | | 193.0–194.5 | 1675 |
| 12 | | 154.0–156.0 | 1660–1690 |
| 13 | | 243.0–244.0 | 1670 |
| 14 | | 171.0–172.0 | 1680–1665 |
| 15 | | 172.0–174.5 | 1685, 1660 |
| 16 | | 193.0–195.5 | 1690, 1660 |
| 17 | ¼ H$_2$O | 199.0–201.0 | 1680, 1650 |
| 18 | | 219.5–221.0 | 1665 |
| 19 | | 227.5–229.5 | 1660 |
| 20 | | 240.0–241.0 | 1665 |
| 21 | | 233.0–235.0 | 1655 |
| 22 | | 241.8–242.3 | 1660 |

TABLE 3-2

| Compound No. | Form | NMR (ppm) |
|---|---|---|
| 1 | | 1.4–2.6, 2.8–3.3, 3.8, 3.95, 4.35, 4.3–4.7, 6.6–7.4, 7.5–7.8, 8.07 |
| 2 | | 1.4–2.6, 2.75–3.4, 3.75, 4.35, 4.0–4.8, 6.05, 6.5–7.35, 7.35–7.80, 8.1 |
| 3 | | 1.55–3.7, 3.90, 3.93, 4.40, 4.45–5.0, 6.55–7.8 |
| 4 | | 1.5–4.0, 4.35, 4.2–4.8, 5.93, 6.50–7.4, 7.85 |
| 5 | | 1.3(d), 1.46–3.3, 3.95, 4.3, 4.0–4.7, 6.6–7.35, 7.55–7.95, 8.25 |
| 6 | ½ H$_2$O | 0.8(d), 1.45–3.35, 3.87, 3.90, 4.0–4.8, 4.4, 6.6–7.4, 8.05 |
| 7 | | 1.27–2.40, 2.50(d), 2.83–3.30, 3.70, 3.83, 4.33, 6.53–7.40, 9.17 |
| 8 | ½ EtOH | 1.55–3.35, 3.80, 3.93, 4.30, 5.65, 6.7–7.9 |
| 9 | ½ EtOH | 1.46–3.50, 3.76, 4.26, 6.03, 6.76–7.75 |
| 10 | | 1.53–3.64, 3.90, 3.93, 4.3, 4.75(trip), 3.64–4.4, 5.65, 6.8–7.6 |
| 11 | | 1.53–3.50, 3.50–4.15, 4.27, 4.65(trip), 5.70, 5.90, 6.56–7.46 |
| 12 | | 1.30(d), 1.53–3.33, 3.97, 4.27, 5.90, 6.7–8.0 |
| 13 | | 0.80(d), 1.7–3.3, 3.87, 3.90, 4.0–4.37, 5.63, 6.7–7.3 |
| 14 | | 1.43–2.53, 2.73–3.27, 3.73, 4.27, 4.1–4.7, 6.6–8.1, 8.17 |
| 15 | | 1.20–2.60, 2.80–3.27, 3.85, 4.20(broad), 4.30, 6.70–8.00, 9.15 |
| 16 | | 1.25–2.47, 2.53–3.10, 3.85, 4.2(broad), 4.33, 6.63–8.17, 9.20 |
| 17 | ¼ H$_2$O | 1.47–2.70, 2.93–3.37, 3.80, 3.87, 4.37, 6.7–8.1 |
| 18 | | 1.50–3.50, 4.37, 4.20–4.90, 6.60–7.50, 7.73 |
| 19 | | 1.20–2.30, 2.47(d), 2.80–3.20, 3.80–4.50, 4.30, 4.50–4.90, 5.07, 6.63–7.43, 9.20 |
| 20 | | 1.10–2.30, 2.47(d), 2.80–3.20, 3.80–4.50, 4.30, 4.50–4.90, 5.07, 6.63–7.50, 7.43, 9.20 |
| 21 | | 1.20–2.30, 2.43(d), 2.80–3.20, 3.75, 3.80–4.50, 4.30, 4.50–5.03, 6.65–7.45, 10.17 |
| 22 | | 1.20–2.27, 2.47(d), 2.80–3.27, 3.80–4.53, 4.30, 4.53–4.97, 5.22, 6.65–7.80, 9.15 |

TABLE 3-3

| Compound No. | Rational formula | | Elementary Analysis (%) | | |
|---|---|---|---|---|---|
| | | | C | H | N |
| 1 | C$_{23}$H$_{27}$N$_3$O$_4$ | A | 67.46 | 6.65 | 10.26 |
| | | F | 67.38 | 6.84 | 10.18 |
| 2 | C$_{22}$H$_{23}$N$_3$O$_4$ | A | 67.16 | 5.89 | 10.68 |
| | | F | 67.15 | 5.84 | 10.54 |
| 3 | C$_{23}$H$_{29}$N$_3$O$_4$ | A | 67.13 | 7.10 | 10.21 |
| | | F | 66.96 | 7.13 | 10.17 |
| 4 | C$_{22}$H$_{25}$N$_3$O$_4$ | A | 66.82 | 6.37 | 10.63 |
| | | F | 66.56 | 6.27 | 10.51 |
| 5 | C$_{24}$H$_{29}$N$_3$O$_4$ | A | 68.07 | 6.90 | 9.92 |
| | | F | 67.91 | 6.84 | 9.90 |
| 6 | C$_{24}$H$_{31}$N$_3$O$_4$·½H$_2$O | A | 66.34 | 7.42 | 9.67 |
| | | F | 66.48 | 7.54 | 9.36 |
| 7 | C$_{24}$H$_{31}$N$_3$O$_5$ | A | 65.29 | 7.08 | 9.52 |
| | | F | 65.17 | 7.07 | 9.41 |
| 8 | C$_{23}$H$_{27}$N$_3$O$_4$·EtOH | A | 66.65 | 6.99 | 9.72 |
| | | F | 66.72 | 6.65 | 9.80 |
| 9 | C$_{22}$H$_{23}$N$_3$O$_4$·½EtOH | A | 66.33 | 6.29 | 10.09 |
| | | F | 66.46 | 6.08 | 10.29 |
| 10 | C$_{23}$H$_{29}$N$_3$O$_4$ | A | 67.13 | 7.10 | 10.21 |
| | | F | 66.85 | 7.25 | 10.01 |
| 11 | C$_{22}$H$_{25}$N$_3$O$_4$ | A | 66.82 | 6.37 | 10.63 |
| | | F | 66.60 | 6.41 | 10.51 |
| 12 | C$_{24}$H$_{29}$N$_3$O$_4$ | A | 68.07 | 6.90 | 9.92 |
| | | F | 67.96 | 6.97 | 9.76 |
| 13 | C$_{24}$H$_{31}$N$_3$O$_4$ | A | 67.74 | 7.34 | 9.87 |
| | | F | 67.60 | 7.39 | 9.71 |
| 14 | C$_{21}$H$_{23}$N$_3$O$_2$ | A | 72.18 | 6.63 | 12.03 |
| | | F | 71.95 | 6.64 | 11.90 |
| 15 | C$_{21}$H$_{22}$N$_3$O$_2$Cl | A | 65.71 | 5.78 | 10.95 |
| | | F | 65.83 | 5.74 | 10.75 |
| 16 | C$_{21}$H$_{22}$N$_3$O$_2$Cl | A | 65.71 | 5.78 | 10.95 |
| | | F | 65.44 | 5.74 | 10.86 |
| 17 | C$_{22}$H$_{25}$N$_3$O$_3$·¼H$_2$O | A | 68.82 | 6.70 | 10.94 |
| | | F | 68.78 | 6.61 | 10.83 |

TABLE 3-3-continued

| Compound No. | Rational formula | | Elementary Analysis (%) | | |
|---|---|---|---|---|---|
| | | | C | H | N |
| 18 | $C_{21}H_{25}N_3O_2$ | A | 71.77 | 7.17 | 11.96 |
| | | F | 71.54 | 7.24 | 11.76 |
| 19 | $C_{21}H_{24}N_3O_2Cl$ | A | 65.36 | 6.27 | 10.89 |
| | | F | 65.44 | 6.27 | 10.62 |
| 20 | $C_{21}H_{24}N_3O_2Cl$ | A | 65.36 | 6.27 | 10.89 |
| | | F | 65.09 | 6.26 | 10.93 |
| 21 | $C_{22}H_{27}N_3O_3$ | A | 69.27 | 7.13 | 11.02 |
| | | F | 69.11 | 7.14 | 11.18 |
| 22 | $C_{21}H_{23}N_3O_2Cl_2$ | A | 60.01 | 5.51 | 10.00 |
| | | F | 59.88 | 5.46 | 9.73 |

A: Calculated, F: Found

Hypotensive activity and acute toxicity of Compound [I] are illustrated below as experiments.

EXPERIMENT 1

This experiment is conducted according to the method described in "Spontaneously Hypertensive Rats (SHR) Guidelines for Breeding, Care and Use" (published by SHR Conference) (1976) p. 11.

Five spontaneously hypertensive rats (15 weeks old, 180 mmHg or more in blood pressure) are used as one group. Each of test compound Nos. 1–22 is added to 0.3% (W/V) CMC aqueous solution in a concentration of 3 mg/ml. Each of the mixtures is orally administered to the rats in a dose 1 mg/100 g. Changes in blood pressure are measured according to the method of tail artery plethysmography (see the literature cited above). The maximum reduction (mmHg) in blood pressure after the administration on the basis of the pressure immediately before the administration is shown in Table 4.

TABLE 4

| Compound No. | Maximum reduction in blood pressure (mmHg) | Compound No. | Maximum reduction in blood pressure (mmHg) |
|---|---|---|---|
| 1 | 29 | 12 | 26 |
| 2 | 40 | 13 | 15 |
| 3 | 32 | 14 | 23 |
| 4 | 41 | 15 | 27 |
| 5 | 22 | 16 | 37 |
| 6 | 24 | 17 | 48 |
| 7 | 28 | 18 | 55 |
| 8 | 18 | 19 | 27 |
| 9 | 17 | 20 | 41 |
| 10 | 10 | 21 | 55 |
| 11 | 18 | 22 | 45 |

EXPERIMENT 2

Three male dd-strain mice (weight 20±1 g) are used for each test compound.

Each of the compounds is added to aqueous physiological sodium chloride, and the mixture is orally (P.O.) administered to the mice in a dose of 1000 mg/kg. After the observation for 7 days, the numbers of deaths are counted, and the results are shown in Table 5.

TABLE 5

| Compound No. | Number of deaths | Compound No. | Number of deaths |
|---|---|---|---|
| 18 | 0/3 | 21 | 1/3 |
| 20 | 0/3 | 22 | 1/3 |

Now, the processes for preparing Compound [I] are described below.

Compound [I] may be prepared by reacting a piperidine derivative represented by the general formula [II]:

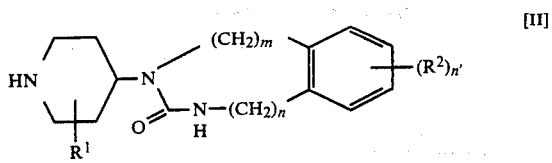

(wherein m, n, n', $R^1$ and $R^2$ have the same meaning as defined above in Formula [I]) or Compound [II] wherein $R^2$ is protected, with a compound represented by the general formula [III]

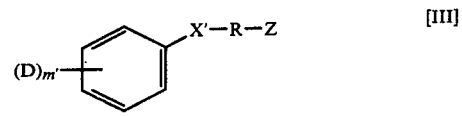

(wherein D, m' and R have the same meaning as defined above in Formula [I], X' is oxygen, sulfur, carbonyl or methylene; and Z is halogen or an eliminable group) or Compound [III] wherein D is protected, and further if necessary, by reducing the resulting product and if necessary, by eliminating the protective group therefrom.

In the definition of Z, halogen includes chlorine, bromine or iodine; and the eliminable group includes alkylsulfonyloxy (for example, methanesulfonyloxy), arylsulfonyloxy (for example, benzenesulfonyloxy, p-toluenesulfonyloxy), etc.

The reaction of Compound [II] or the protected one with Compound [III] or the protected one is carried out in an inert solvent. Ketone (e.g. acetone), halogenated hydrocarbon (e.g. chloroform and methylene chloride), amide (e.g. dimethylformamide), sulfoxide (e.g. dimethylsulfoxide), substituted or unsubstituted aromatic hydrocarbon (e.g. benzene, toluene and chlorobenzene), lower alcohol (e.g. methanol, ethanol and isopropanol), etc. may be used alone or in combination as an inert solvent. The reaction is carried out at 0°–150° C., preferably at a temperature between room temperature and the boiling point of the solvent depending on the reactivity of the group Z which is exchangeable. The reaction usually proceeds very smoothly in the presence of a base such as lower alcoholate (e.g. sodium methylate and sodium ethylate), alkali hydroxide (e.g. sodium hydroxide), alkali carbonate (e.g. sodium carbonate and potassium carbonate), tertiary amine (e.g. triethylamine and pyridine), etc. The amount of the base is usually 1.0 to 1.2 times the equivalent amount based on Compound [II]. When an acid addition salt of Compound [II] such as hydrochloride is used, it goes without saying that the base supplementary enough to neutralize the acid is added thereto. Use of reaction-promoting agents such as potassium iodide is preferable for smooth proceeding of the reaction.

When either $R^2$ or D, or both is (are) hydroxy, amino or lower alkylamino, these groups are protected in a conventional manner prior to the above reaction. After completion of the reaction, the protective group is eliminated in a conventional manner to obtain the desired product.

When X' is carbonyl, the resulting product is reduced to obtain Compound [I] wherein X is hydroxymethylene. The reaction may be carried out by reacting Compound [I] wherein X is carbonyl with a complex metal hydride such as sodium borohydride in a lower alcohol such as methanol, ethanol and isopropanol at −10° to 100° C., preferably at a temperature between 0° C. and the boiling point of the used solvent. Alternatively, the reaction may be carried out by subjecting Compound [I] wherein X is carbonyl to catalytic reduction using hydrogenating catalyst such as palladium carbon in lower alcohol such as methanol and ethanol, lower aliphatic acid such as acetic acid, water or a mixed solvent thereof. These reactions may be carried out in an open vessel or in a closed vessel under pressure.

A starting compound of Compound [I], Compound [II] is also new compound.

Compounds represented by the general formula [II'], which is a Compound [II] wherein m is 1 and n is 0:

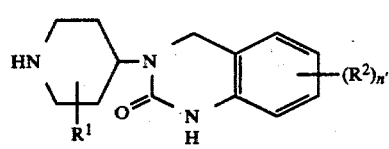

(wherein n', R¹ and R² have the same definition as given in formula [I] above), may be prepared in the following manner. First, a 4-aminopiperidine derivative represented by the general formula [IV]:

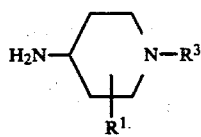

(wherein R¹ represents the same groups as defined above and R³ is a protective group for amino group) is reacted with a compound represented by the general formula [V]:

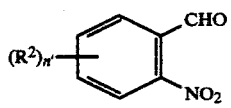

(wherein n' and R² represent the same groups as defined above) to prepare a compound represented by the general formula [VI]:

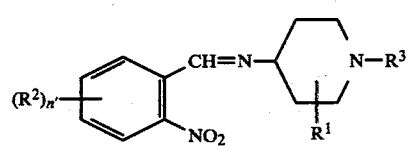

(wherein n', R¹, R² and R³ represent the same groups as defined heretofore).

R³ in Compound [IV] includes acyl (e.g. acetyl and benzoyl), alkyloxycarbonyl (e.g. t-butoxycarbonyl and ethoxycarbonyl), benzyl, tosyl, etc.

The above reaction may be carried out without solvent or in a lower alkanol (e.g. methanol, ethanol and propanol), aromatic hydrocarbon (e.g. benzen, toluene and xylene), halogenated hydrocarbon (e.g. methylene chloride and chloroform) or a mixed solvent thereof.

When the reaction is carried out in an alkanol, the subsequent conversion of Compound [VI] to a compound represented by the general formula [VII] may conveniently be carried out without isolating Compound [VI].

Compound [V] as a starting compound is usually used in 1.0 to 1.2 times equivalent amounts, preferably in 1.0 time the equivalent amount based on Compound [IV].

The reaction proceeds at room temperature in a short time, if mecessary, with heating.

Next, Compound [VI] is reduced using a complex metal hydride such as sodium borohydride and sodium cyanohydride in lower alkanol such as methanol, ethanol and isopropanol to prepare a 4-substituted piperidine derivative represented by the general formula [VII]:

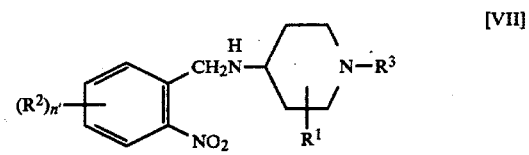

(wherein n', R¹, R² and R³ have the same meaning as defined above). The reaction is carried out at −10° to 100° C., preferably 0° C. to room temperature.

Compound [VII] is reduced to prepare a compound represented by the general formula [VIII]:

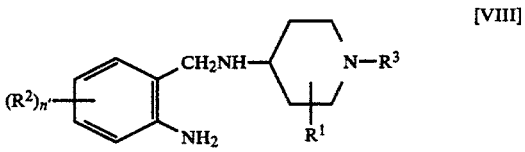

(wherein n', R¹, R² have the same meaning as defined above).

The reaction may be carried out according to a conventional method used in reduction of nitro group to amino group, for example, reduction using metal (e.g. Sn, Fe and Zn), mineral acid (e.g. hydrochloric acid and sulfuric acid) or organic acid (e.g. acetic acid), reduction using sulfide or hydrazine or catalytic reduction using palladium carbon, etc.

When the catalytic reduction is applied, the reaction is carried out by reacting Compound [VII] with hydrogen in an equivalent amount in water, lower alkanol (such as methanol and ethanol) or a mixed solvent thereof at a temperature of 20° to 60° C., preferably at room temperature.

Compound [VIII] is reacted with a carbonic acid derivative such as phosgene, trichloromethyl chloroformate, alkyl chloroformate, 1,1'-carbonyldiimidazole and urea to prepare a compound represented by the general formula [IX]:

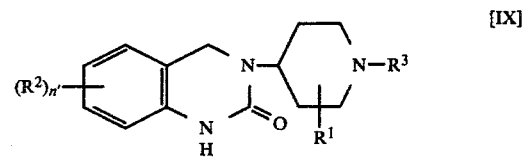

(wherein n', R¹, R² and R³ have the same meaning as defined above).

All of the above reactions can be carried out according to conventional methods and the reaction wherein 1,1′-carbonyldiimidazole is used is particularly described hereinafter. The reaction is carried out in an aprotic polar solvent such as halogenated hydrocarbon (.e.g. methylene chloride and chloroform), ether (e.g. ethyl ether, tetrahydrofuran and dioxane), acetonitrile, dimethylformamide and dimethylsulfoxide, in combination thereof or alone, preferably with stirring. Preferably, the amount of 1,1′-carbonyldiimidazole is 1.0 to 2.0 times the equivalent amount based on Compound [VIII]. The reaction is carried out at a temperature of from room temperature to the boiling point of the used solvent. The reaction is usually completed in 1 to 3 hours when treated at the boiling point of the solvent and is completed in 10 to 15 hours, when treated at room temperature.

Finally, Compound [IX] is subjected to the usual reaction of eliminating the protective group from amino group whereby the compound is converted to Compound [II′]. The elimination method when the protective group R³ is benzyl is described below.

The elimination of benzyl is carried out by subjecting Compound [IX] to catalytic reduction in the presence of the catalyst for catalytic reduction such as palladium catalyst, e.g. palladium/carbon in lower alcohol such as methanol, ethanol and isopropanol, water, or a mixed solvent thereof. The reaction is preferably carried out in the coexistence of a mineral acid such a hydrochloric acid, hydrobromic acid, hydroiodic acid and perchloric acid, whose amount is preferably 1 to 2 times the equivalent amount based on Compound [IX]. The reaction is carried out at room temperature to 50° C.

Piperidine derivatives represented by the general formula [II″], which is a Compound [II] wherein m is 0 and n is 1, (Compound [II] is a starting compound for the synthesis of Compound [I]):

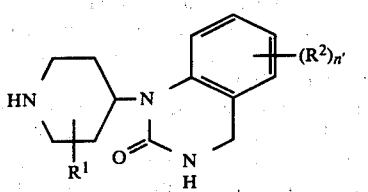

[II″]

(wherein n′, R¹ and R² have the same meaning as defined above) may be prepared as follows.

First, a 4-oxopiperidine derivative represented by the general formula [X]:

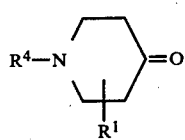

[X]

(wherein R¹ has the same meaning as defined above and R⁴ is unsubstituted or substituted benzyl, arylsulfonyl, alkylsulfonyl or t-butoxycarbonyl) is reacted with a compound represented by the general formula [XI]:

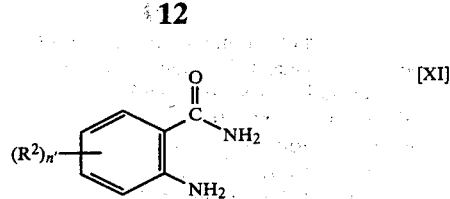

[XI]

(wherein n′ and R² have the same meanings as defined above) in the presence of sulfuric acid, alkanesulfonic acid such as methanesulfonic acid or arylsulfonic acid such as p-toluenesulfonic acid as a catalyst in an aromatic hydrocarbon solvent such as benzene, toluene and xylene to prepare a compound represented by the general formula [XII]:

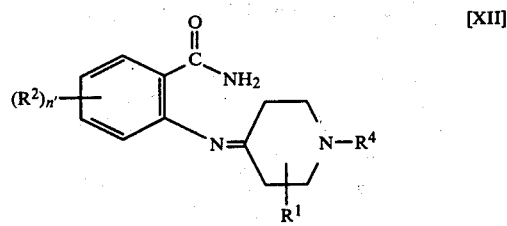

[XII]

(wherein n′, R¹, R² and R⁴ have the same meanings as defined above). The above reaction is preferably carried out distilling off water under reflux condition in the presence of p-toluenesulfonic acid.

Compound [XII] is then reduced with a complex metal hydride, preferably lithium aluminum hydride in an ether solvent such as ethyl ether, dioxane and tetrahydrofuran to prepare a compound represented by the general formula [XIII]:

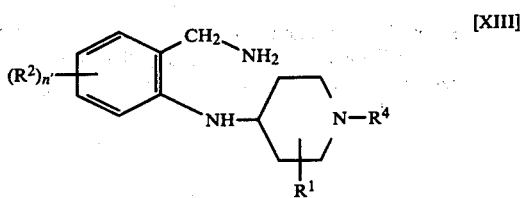

[XIII]

(wherein n′, R¹, R² and R⁴ have the same meanings as defined above).

Finally, Compound [XIII] may be converted to Compound [II″] according to the similar manner to that described in the case where Compound [VIII] is converted to Compound [II′] through Compound [IX].

Isolation and purification of Compound [I], as well as the above-mentioned intermediates, are carried out according to conventional methods in the field of organic synthetic chemistry, for example, concentration, extraction, recrystallization and chromatography. Specifically, since Compound [I] readily crystallizes in general, it can be isolated and purified by distilling off the solvent from the reaction mixture and recrystallizing the residue from a suitable solvent such as ethanol.

A pharmacologically acceptable acid addition salt of Compound [I] may be obtained by reacting Compound [I] with a suitable acid in a suitable solvent such as ethanol.

The pharmaceutical compositions of the present invention are described below.

It is obvious from the foregoing various experimental data that Compound [I] has a hypotensive activity.

In view of the hypotensive activity, the compounds of the present invention may be used in various pharmaceutical forms for administration. Pharmaceutical compositions of the present invention are prepared by uniformly mixing an effective amount of the compound in the form of a base or an acid addition salt as an active ingredient with a pharmaceutically acceptable carrier. According to the pharmaceutical forms suitable for administration, the carrier may take various forms. It is desirable that the pharmaceutical compositions are in single administration form suitable for administration per os or by injection.

In preparation of the compositions for oral administration, any useful pharmaceutical carrier may be used. For example, water, glycols, oils, alcohols, etc. may be used to prepare oral liquid preparations such as suspensions and syrups, and excipients, lubricants, binders, disintegrators, etc. may be used to prepare powders, pills, capsules and tablets. Examples of the carriers are glucose and lactose as the excipients, starch and sodium alginate as the disintegrators, magnesium stearate, paraffin sulfate and talc as the lubricants, and syrup, ethanol and gelatin as the binders. The active ingredient is orally administered in a dose of 1–100 mg, particularly 10–60 mg, per day for an adult.

The preparation of Compound [I] and the present pharmaceutical compositions are illustrated by the following examples, and the preparation of the intermediates is illustrated by the following reference examples.

EXAMPLE 1

1-(3,4-Dimethoxybenzoylmethyl)-4-(3,4-dihydro-2(1H)-quinazolinon-3-yl]-piperidine In this example, 2.31 g of 4-[3,4-dihydro-2(1H)-quinazolinon-3-yl]-piperidine, 2.59 g of ω-bromo-3,4-dimethoxyacetophenone, 1.01 g of triethylamine and 70 ml of chloroform are mixed and stirred at room temperature for 8 hours. Then, the resultant solution is concentrated to dryness. The residual crystals are mixed with water, then separated therefrom by filtration and dried to obtain 3.80 g of a crude product. The crude product is recrystallized from hot ethanol to obtain 3.17 g of the desired product.

EXAMPLE 2

1-(3,4-Methylenedioxybenzoylmethyl)-4-[3,4-dihydro-2(1H)-quinazolinon-3-yl]-piperidine In this example, the procedure of Example 1 is repeated except that 2.31 g of 4-[3,4-dihydro-2(1H)-quinazolinon-3-yl]-piperidine and 2.43 g of ω-bromo-3,4-methylenedioxyacetophenone is used to produce a crude product. The crude product is recrystallized from hot ethanol to obtain 3.18 g of the desired product.

EXAMPLE 3

1-[2-(3,4-Dimethoxyphenyl)-2-hydroxyethyl]-4-[3,4-dihydro-2(1H)-quinazolinon-3-yl]-piperidine In this example 2.80 g of 1-(3,4-dimethoxybenzoylmethyl)-4-[3,4-dihydro-2(1H)-quinazolinon-3-yl]-piperidine and 150 ml of methanol are mixed and stirred at room temperature. Then, 460 mg of sodium borohydride is added to the stirred mixture over a period of 30 minutes. Thereafter, the mixture is stirred overnight at room temperature. The white crystals deposited are separated by filtration, successively washed with methanol and water and dried to obtain 2.02 g of a crude product. The crude product is crystallized from hot ethanol to obtain 1.86 g of the desired product.

EXAMPLE 4

1-[2-(3,4-Methylenedioxyphenyl)-2-hydroxyethyl]-4-[3,4-dihydro-2(1H)-quinazolinon-3-yl]-piperidine In this example, the procedure of Example 3 is repeated except that 2.2 g of 1-(3,4-methylenedioxybenzoylmethyl)-4-[3,4-dihydro-2(1H)-quinazolinon-3-yl]-piperidine and 410 mg of sodium borohydride are used to obtain 1.69 g of a crude product. The crude product is recrystallized from hot ethanol to obtain 1.50 g of the desired product.

EXAMPLE 5

1-[1-(3,4-Dimethoxybenzoyl)-ethyl]-4-[3,4-dihydro-2(1H)-quinazolinon-3-yl]-piperidine In this example, 3.46 g of 4-[3,4-dihydro-2(1H)-quinazolinon-3-yl]-piperidine, 4.10 g of α-bromo-3,4-dimethoxypropiophenone, 2.1 ml of triethylamine and 30 ml of dimethylformamide are mixed and stirred at room temperature for a half and 2 hours. Then, the reaction solution is poured into 150 ml of ice water and the mixture is stirred for 30 minutes. The white crystals deposited are separated by filtration, washed with water and dried to obtain 5.87 g of a crude product. The crude product is recrystallized from hot ethanol to obtain 4.44 g of the desired product.

EXAMPLE 6

1-[3-(3,4-Dimethoxyphenyl)-3-hydroxypropyl-2]-4-[3,4-dihydro-2(1H)-quinazoline-3-yl]-piperidine In this example, 3.0 g of 1-[1-(3,4-dimethoxybenzoyl)-ethyl]-4-[3,4-dihydro-2(1H)-quinazolinon-3-yl]-piperidine and 150 ml of methanol are mixed and stirred under ice-cooling. Then, 1.50 g of sodium borohydride is added to the stirred mixture over a period of 3 hours. Thereafter, the mixture is stirred overnight at room temperature. Then, the white crystals deposited are separated by filtration, successively washed with methanol and water and dried to obtain 2.03 g of a crude product. On the other hand, the filtrate is concentrated and mixed with water. The white crystals deposited are separated by filtration, washed with water and dried to obtain 0.77 g of a crude product. The crude products are combined and recrystallized from hot ethanol to obtain 2.08 g of the desired product.

EXAMPLE 7

1-[2-(3,4,5-Trimethoxyphenyl)-2-hydroxyethyl]-4-[3,4-dihydro-2(1H)-quinazolinon-3-yl]-piperidine In this example, 3.47 g of 4-[3,4-dihydro-2(1H)-quinazolinon-3-yl]-piperidine, 4.33 g of ω-bromo-3,4,5-trimethoxyacetophenone, 2.1 ml of triethylamine and 100 ml of methanol are mixed and stirred at room temperature for one hour and 40 minutes. Then, the reaction solution is concentrated and the resulting residue is crystallized by addition of water. The crystals are separated by filtration, washed with water and dried to obtain 6.50 g of crude crystals of 1-(3,4,5-trimethoxybenzoyl)-4-[3,4-dihydro-2(1H)-quinazolinon-3-yl]-piperidine. Then, 3.20 g of the crude crystals is suspended in 150 ml of methanol and the suspension is stirred under ice-cooling. Then, 2.5 g of sodium borohydride is added to the stirred suspension over a period of 3 hours. Thereafter, the resultant mixture is brought back to room temperature and then stirred overnight. The white crystals deposited are separated by filtration, successively washed with methanol and water, and dried to obtain 2.27 g of a crude product. The crude product is recrystallized from a mixed solvent of chloroform and ethanol to obtain 1.86 g of the desired product.

EXAMPLE 8

1-(3,4-Dimethoxybenzoylmethyl)-4-[3,4-dihydro-2(1H)-quinazolinon-1-yl]-piperidine In this example, the procedure of Example 1 is repeated except that 2.77 g of 4-[3,4-dihydro-2(1H)-quinazolinon-1-yl]-piperidine, 3.11 g of ω-bromo-3,4-dimethoxyacetophenon and 1.21 g of triethylamine are used to obtain 4.15 g of a crude product. The crude product is recrystallized from hot ethanol to obtain 2.58 g of the desired product.

EXAMPLE 9

1-(3,4-Methylenedioxybenzoylmethyl)-4-[3,4-dihydro-2(1H)-quinazolinon-1-yl]-piperidine In this example, 3.46 g of 4-[3,4-dihydro-2(1H)-quinazolinon-1-yl]-piperidine, 3.64 g of ω-bromo-3,4-methylenedioxyacetophenone, 2.1 ml of triethylamine and 30 ml of dimethylformamide are mixed and stirred at room temperature for 3 hours. The resultant solution is poured into ice water. The crystals deposited are separated by filtration, washed with water and dried to obtain 5.23 g of a crude product. The crude product is recrystallized from hot ethanol to obtain 3.87 g of the desired product.

EXAMPLE 10

1-[2-(3,4-Dimethoxyphenyl)-2-hydroxyethyl]-4-[3,4-dihydro-2(1H)-quinazolinon-B 1-yl]-piperidine In this example, 2.20 g of 1-(3,4-dimethoxybenzoylmethyl)-4-[3,4-dihydro-2(1H)-quinazolinon-1-yl]-piperidine and 150 ml of methanol are mixed and stirred at room temperature. To the stirred mixture, 200 mg of sodium borohydride is added over a period of 30 minutes. Thereafter, the mixture is stirred at room temperature overnight and the resultant reaction solution is concentrated. The residue is mixed with water. The crystals deposited are separated by filtration, washed with water and dried to obtain 1.68 g of a crude product. The crude product is recrystallized from hot ethanol to obtain 1.23 g of the desired product.

EXAMPLE 11

1-[2-(3,4-Methylenedioxyphenyl)-2-hydroxyethyl]-4-[3,4-dihydro-2(1H)-quinazolinon-1-yl]-piperidine In this example, 2.70 g of 1-(3,4-methylenedioxybenzoylmethyl)-4-[3,4-dihydro-2(1H)-quinazolinon-1-yl]-piperidine and 150 ml of methanol are mixed and stirred under ice-cooling. Then, 2.0 g of sodium borohydride is added to the stirred mixture over a period of one hour. Subsequently, the mixture is brought back to room temperature and stirred for 3 hours at room temperature and the reaction solution is concentrated. The resultant residue is mixed with 50 ml of water and the mixture is extracted with ethyl acetate (100 ml×2 and 50 ml×1). The extract is washed with water, dried and concentrated. The resultant viscous residue is mixed with 5 ml of methanol. The crystals deposited are separated by filtration, washed with methanol and dried to obtain 2.05 g of a crude product. The crude product is recrystallized from hot ethanol to obtain 1.74 g of the desired product.

EXAMPLE 12

1-[1-(3,4-Dimethoxybenzoyl)-ethyl]-4-[3,4-dihydro-2(1H)-quinazolinon-1-yl]-piperidine In this example, 3.46 g of 4-[3,4-dihydro-2(1H)-quinazolinon-1-yl]-piperidine, 4.10 g of α-bromo-3,4-dimethoxypropiophenone, 2.1 ml of triethylamine and 30 ml of dimethylformamide are mixed and stirred for 3 hours at room temperature. Then, the resultant solution is poured into ice water. The insoluble substance deposited is separated by filtration, washed with water and mixed with methanol. The crystals deposited are separated by filtration, washed with methanol and dried to obtain 4.68 g of a crude product. On the other hand, the water layer is further extracted with chloroform and the organic layer is washed with water, dried and concentrated. The residue is mixed with 2 ml of methanol. The resultant crystals are separated by filtration and dried to obtain 0.46 g of a crude product. These crude products are combined and recrystallized from hot ethanol to obtain 3.73 g of the desired product.

EXAMPLE 13

1-[3-(3,4-Dimethoxyphenyl)-3-hydroxypropyl-2-]-4-[3,4-dihydro-2(1H)-quinazolinon-1-yl]-piperidine In this example, 2.70 g of 1-[1-(3,4-dimethoxybenzoyl)-ethyl]-4-[3,4-dihydro-2(1H)-quinazolinon-1-yl]-piperidine and 150 ml of methanol are mixed and stirred under ice-cooling. Then, 2.0 g of sodium borohydride is added to the stirred mixture over a period of one hour. The resultant mixture is brought back to room temperature and stirred at room temperature for 3 hours. The white crystals deposited are separated by filtration, successively washed with methanol and water and dried to obtain 2.07 g of a crude product. This crude product is recrystallized from a mixed solvent of chloroform and ethanol to obtain 1.87 g of the desired product.

EXAMPLE 14

1-Benzoylmethyl-4-[3,4-dihydro-2(1H)-quinazolinon-3-yl]-piperidine

In this example, 4.0 g of 4-[3,4-dihydro-B 2(1H)-quinazolinon-3-yl]-piperidine mono-hydrochloride, 3.0 g of ω-bromoacetophenone, 4.2 ml of triethylamine and 60 ml of methanol are mixed and stirred at room temperature overnight. Then, the white crystals deposited are separated by filtration, successively washed with methanol and water and dried to obtain 4.38 g of a crude product. The crude product is recrystallized from chloroform-ethanol to obtain 3.40 g of the desired product.

EXAMPLE 15

1-(3-Chlorobenzoylmethyl)-4-[3,4-dihydro-2(1H)-quinazolinon-3-yl]-piperidine

In this example, 2.67 g of 4-[3,4-dihydro-2(1H)-quinazolinon-3-yl]-piperidine mono-hydrochloride, 2.33 g of α-bromo-m-chloroacetophenone, 2.8 ml of triethylamine and 30 ml of methanol are mixed and stirred at room temperature overnight. Then, the white crystals deposited are separated by filtration, successively washed with methanol and water and dried to obtain 2.89 g of a crude product. The crude product is recrystallized from a mixed solvent of chloroform and ethanol to obtain 1.93 g of the desired product.

EXAMPLE 16

1-(4-Chlorobenzoylmethyl)-4-[3,4-dihydro-2(1H)-quinazolinon-3-yl]-piperidine

In this example, 4.0 g of 4-[3,4-dihydro-2(1H)-quinazolinon-3-yl]-piperidine mono-hydrochloride, 3.5 g of α-bromo-p-chloroacetophenone, 4.2 ml of triethylamine and 60 ml of methanol are mixed and stirred at room temperature overnight. The white crystals deposited are separated by filtration, successively washed with methanol and water and dried to obtain 5.17 g of a crude product. The crude product is recrystallized from a mixed solvent of chloroform and ethanol to obtain 3.21 g of the desired product.

EXAMPLE 17

1-(4-Methoxybenzoylmethyl)-4-[3,4-dihydro-2(1H)-quinazolinon-3-yl]-piperidine

In this example, 4.00 g 4-[3,4-dihydro-2(1H)-quinazolinon-3-yl]-piperidine mono-hydrochloride, 3.44 g of α-bromo-p-methoxyacetophenone, 4.2 ml of triethylamine and 60 ml of methanol are mixed and stirred at room temperature overnight. Then, the white crystals deposited are separated by filtration, successively washed with methanol and water and dried to obtain 4.71 g of a crude product. The crude product is recrystallized from a mixed solvent of chloroform and ethanol to obtain 3.79 g of the desired product.

EXAMPLE 18

1-(2-Phenyl-2-hydroxyethyl)-4-[3,4-dihydro-2(1H)-quinazolinon-3-yl]-piperidine

In this example, 2.30 g of 1-benzoylmethyl-4-[3,4-dihydro-2(1H)-quinazolinon-3-yl]-piperidine and 100 ml of methanol are mixed and stirred at room temperature. To the stirred mixture, 1.5 g of sodium borohydride is added over a period of 5 hours. Then, the mixture is stirred overnight at room temperature. The white crystals deposited are separated by filtration, successively washed with methanol and water and dried to obtain 2.06 g of a crude product. The crude product is recrystallized from a mixed solvent of chloroform and ethanol to obtain 1.47 g of the desired product.

EXAMPLE 19

1-[2-(3-Chlorophenyl)-2-hydroxyethyl]-4-[3,4-dihydro-2(1H)-quinazolinon-3-yl]-piperidine In this example, 1.50 g of 1-(3-chlorobenzoylmethyl)-4-[3,4-dihydro-2(1H)-quinazolinon-3-yl]-piperidine and 75 ml of methanol are mixed and stirred at room temperature. To the stirred mixture, 1.0 g of sodium borohydride is added over a period of 5 hours. Then, the mixture is stirred overnight at room temperature. The white crystals deposited are separated by filtration, successively washed with methanol and water and dried to obtain 1.21 g of a crude product. The crude product is recrystallized from a mixed solvent of chloroform and ethanol to obtain 0.87 g of the desired product.

EXAMPLE 20

1-[2-(4-Chlorophenyl)-2-hydroxyethyl]-4-[3,4-dihydro-2(1H)-quinazolinon-3-yl]-piperidine In this example, 2.70 g of 1-(4-chlorobenzoylmethyl)-4-[3,4-dihydro-2(1H)-quinazolinon-3-yl]-piperidine and 150 ml of methanol are mixed and stirred at room temperature. To the stirred mixture, 2.0 g of sodium borohydride is added over a period of 5 hours. Then, the resultant mixture is stirred overnight at room temperature. The white crystals deposited are separated by filtration, successively washed with methanol and water and dried to obtain 2.07 g of a crude product. The crude product is recrystallized from a mixed solvent of chloroform and ethanol to obtain 1.59 g of the desired product.

EXAMPLE 21

1-[2-(4-Methoxyphenyl)-2-hydroxyethyl]-4-[3,4-dihydro-2(1H)-quinazolinon-3-yl]-piperidine In this example, 2.70 g of 1-(4-methoxybenzoyl)-4-[3,4-dihydro-2(1H)-quinazolinon-3-yl]-piperidine and 150 ml of methanol are mixed and stirred at room temperature. To the stirred mixture, 2.0 g of sodium borohydride is added over a period of 5 hours. Then, the mixture is stirred overnight at room temperature. The white crystals deposited are separated by filtration, successively washed with methanol and water and dried to obtain 2.40 g of a crude product. The crude product is recrystallized from a mixed solvent of chloroform and ethanol to obtain 1.41 g of the desired product.

EXAMPLE 22

1-[2-(3,4-Dichlorophenyl)-2-hydroxyethyl]-4-[3,4-dihydro-2(1H)-quinazolinon-3-yl]-piperidine In this example, 3.20 g of 4-[3,4-dihydro-2(1H)-quinazolinon-3-yl]-piperidine hydrochloride, 3.22 g of ω-bromo-3,4-dichloroacetophenone, 3.36 ml of triethylamine and 48 ml of methanol are mixed and stirred overnight. The resultant crystals are separated by filtration, washed with 5 ml of methanol and dried to obtain 4.55 g of 1-(3,4-dichlorobenzoylmethyl)-4-[3,4-dihydro-2(1H)-quinazolinon-3-yl]-piperidine as crude crystals. Then, 4.00 g of the crude crystals are suspended in 200 ml of ethanol and stirred at room temperature. Then 2.0 g of sodium borohydride is added to the stirred suspension and the mixture is stirred overnight. Further, 1.0 g of sodium borohydride is added to the mixture. The mixture is refluxed with heating for 3 hours and then brought back to room temperature. The resultant white crystals are separated by filtration, successively washed with methanol and water and dried to obtain 3.5 g of a crude product. The crude product is twice recrystallized from a mixed solvent of dimethylformamide and methanol to obtain 1.88 g of the desired product.

EXAMPLE 23

Example of preparing 10,000 5 mg-tablets

| Compound 18 | 50 g |
|---|---|
| Magnesium stearate | 4 g |
| Crystalline cellulose | 746 g |

The above-described ingredients are mixed for 5 minutes by means of a mixer. The resulting mixed powder is made into 10,000 tablets of 6.0 mm in diameter, 2.5 mm in thickness, and 80 mg in weight using a tablet-making machine (Model HU-37; made by Kikusui Seisakusho) equipped with a pestle having a plane surface and round corners.

EXAMPLE 24

| Compound 20 | 55 g |
| Magnesium stearate | 4 g |
| Crystalline cellulose | 741 g |

The above-described ingredients are processed in the same manner as in Example 23 to obtain tablets.

EXAMPLE 25

| Compound 18 | 56 g |
| Magnesium stearate | 4 g |
| Crystalline cellulose | 740 g |

The above-described ingredients are processed in the same manner as in Example 23 to obtain tablets.

EXAMPLE 26

Example of preparing a powder

| Compound 21 | 110 g |
| Lactose | 890 g |

The above-described ingredients are mixed for 10 minutes using a mixer to obtain a uniform mixture (powder).

EXAMPLE 27

| Compound 22 | 109 g |
| Lactose | 891 g |

The above-described ingredients are mixed for 10 minutes using a mixer to obtain a uniform mixture (powder).

REFERENCE EXAMPLE 1

1-Benzyl-4-[N-(o-nitrobenzyl)-amino]-piperidine dihydrochloride

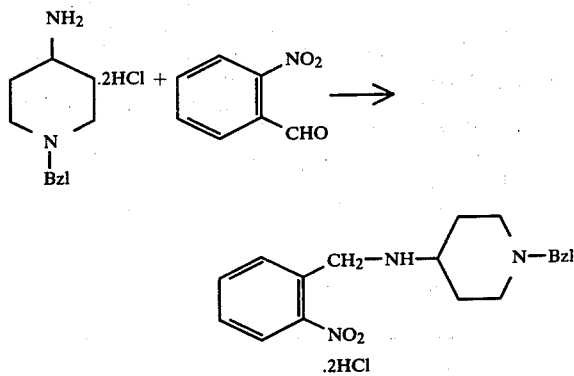

In this reference example, 5.24 g of 1-benzyl-4-amino-piperidine dihydrochloride, 3.02 g of o-nitrobenzaldehyde, 2.02 g of triethylamine and 30 ml of methanol are mixed and stirred at room temperature for one hour. The resultant solution is cooled with ice and stirred. To the stirred solution, 1 g of sodium borohydride is added little by little over a period of one hour. Then, the mixture is brought back to room temperature and stirred at room temperature for 2 hours. The resultant solution is poured into 200 ml of ice water and extracted with ether. The organic layer is washed with water, dried and concentrated. The oily residue is dissolved in 20 ml of ethanol. The solution is mixed with 10 ml of a solution of 5.7 N hydrochloric acid in ethyl acetate. The white crystals deposited are separated by filtration, washed with 20 ml of ethyl acetate and dried to obtain 5.70 g of a crude product. The crude product is recrystallized from hot ethanol to obtain 2.90 g of the desired product.

Melting point: 260.0° to 263.5° C.

| Elementary analysis | H | C | N |
|---|---|---|---|
| Calculated | 6.33 | 57.29 | 10.55 |
| Found | 6.48 | 57.19 | 10.27 |

REFERENCE EXAMPLE 2

1Benzyl-4-[N-o-aminobenzyl)-amino]-piperidine trihydrochloride

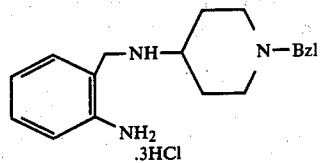

In this reference example, 31.8 g of 1-benzyl-4-[N-(o-nitrobenzyl)-amino]-piperidine dihydrochloride, 3.2 g of 10% Pd-C and 500 ml of water are mixed and stirred at room temperature. Then, about 6 l of hydrogen gas is absorbed by the mixture. Then the reaction is discontinued and the Pd-C is removed by filtration. The aqueous solution is adjusted to pH 11 with an aqueous sodium hydroxide and then extracted with ethyl acetate. The organic layer is washed with water, dried and concentrated. The resulting oily product is dissolved in 140 ml of ethanol. Then, 70 ml of a solution of 5.7 N hydrochloric acid in ethyl acetate is added thereto. The white crystals deposited are separated by filtration, washed with ethyl acetate and dried to obtain 23.5 g of a crude product. The crude product is recrystallized from a mixed solvent of methanol and ethyl acetate to obtain 15.0 g of the desired product.

Melting point: 225.0° to 228.0° C.

| Elementary analysis | H | C | N |
|---|---|---|---|
| Calculated | 6.97 | 56.37 | 10.38 |
| Found | 7.00 | 56.35 | 10.31 |

REFERENCE EXAMPLE 3

1-Benzyl-4-[3,4-dihydro-2(1H)-quinazolinon-3-yl]-piperidine

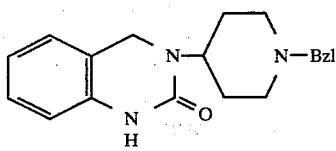

In this reference example, 4.04 g of 1-benzyl-4-[N-(o-aminobenzyl)-amino]-piperidine trihydrochloride, 3.04 g of triethylamine, 2.03 g of 1,1'-carbonyldiimidazole and 50 ml of acetonitrile are mixed and stirred at room temperature for 4 hours. Then, 0.8 g of 1,1'-carbonyldiimidazole is further added to the mixture and the resultant mixture is refluxed with heating for 20 minutes. The solution is cooled to room temperature. The crystals deposited are separated by filtration, washed with water and dried to obtain 2.50 g of a crude product. The crude product is recrystallized from hot ethanol to obtain 1.75 g of the desired product.

Melting point: 204.5° to 205.5° C.

| Elementary analysis | H | C | N |
|---|---|---|---|
| Calculated | 7.21 | 74.74 | 13.07 |
| Found | 7.16 | 75.02 | 13.21 |

REFERENCE EXAMPLE 4

4-[3,4-Dihydro-2(1H)-quinazolinon-3-yl]-piperidine hydrochloride:

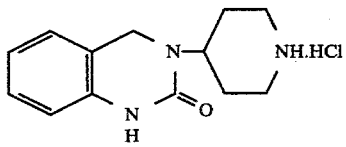

In this reference example, 1.0 g of 1-benzyl-4-[3,4-dihydro-2(1H)-quinazolinon-3-yl]-piperidine, 0.10 g of 10% Pd-C, 10 ml of acetic acid and 10 ml of methanol are mixed and stirred at room temperature. Hydrogen gas is introduced to the stirred mixture for 4 days. Then, the reaction is discontinued and the Pd-C is removed by filtration. The filtrate is concentrated. The resultant oily substance is dissolved in 5 ml of ethanol. Then, 5 ml of a solution of 5.7 N hydrochloric acid in ethyl acetate is added thereto and the resultant mixture is allowed to stand overnight at room temperature. The crystals deposited are separated by filtration, washed with ethyl acetate and dried to obtain 0.74 g of a crude product. The crude product is recrystallized from a mixed solvent of methanol and ethyl acetate to obtain 0.52 g of the desired product.

Melting point: 288.0° to 293.0° C.

| Elementary analysis | H | C | N |
|---|---|---|---|
| Calculated | 6.77 | 58.32 | 15.69 |
| Found | 6.87 | 58.26 | 15.65 |

REFERENCE EXAMPLE 5

1-Benzyl-4-[N-o-aminomethylphenyl)-amino]-piperidine

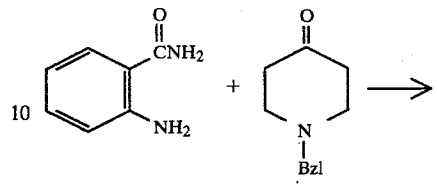

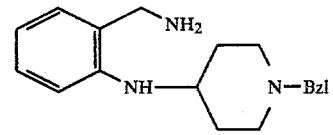

In this reference example, the mixture of 13.6 g of anthranilamide, 18.9 g of 1-benzyl-4-piperidone, 1.0 g of p-toluene-sulfonic acid monohydrate and 200 ml of benzene is refluxed in a Dean Stark apparatus for 6 hours to distill off water. The resultant suspension of the Schiff-base is concentrated. The residue is mixed with 250 ml of dry dioxane to form a suspension. Separately, 100 ml of dry dioxane and 12.4 g of lithium aluminum hydride are mixed. The above Schiff-base suspension is added little by little to the mixture with stirring without cooling. The mixture is stirred for one hour and then refluxed with heating for 18 hours. The reaction solution is cooled to room temperature and poured little by little into 1.3 l of ice water. The resultant suspension is poured little by little into a funnel previously coated with a filter aid and subjected to suction filtration. The cake on the funnel is washed with 500 ml of chloroform and filtered. The organic layer is washed with water, dried and concentrated to obtain 22.9 g of a crude product. The crude product is recrystallized from hot ethanol to obtain 18.7 g of the desired product.

Melting point: 117.0° to 118.0° C.

| Elementary analysis | H | C | N |
|---|---|---|---|
| Calculated | 8.53 | 77.25 | 14.22 |
| Found | 8.66 | 77.45 | 13.98 |

REFERENCE EXAMPLE 6

1-Benzyl-4-[3,4-dihydro-2(1H)-quinazolinon-1-yl]-piperidine

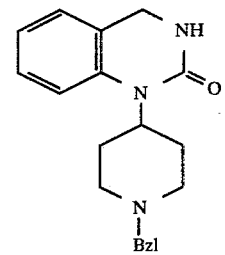

In this reference example, to the mixture of 23.0 g of 1-benzyl-4-[N-(o-aminomethylphenyl)-amino]-piperidine and 200 ml of acetonitrile, 17.4 g of 1,1'-carbonyldiimidazole is added over a period of 3 hours with stirring at 40° to 60° C. Then, the resultant mixture is refluxed with heating for one hour, brought back to room temperature and stirred at room temperature for 2 hours. The crystals deposited are separated by filtration, successively washed with water and methanol and dried to obtain 16.8 g of a crude product. The crude product is recrystallized from methanol to obtain 12.18 g of the desired product.

Melting point: 119.5° to 120.5° C.

| Elementary analysis | H | C | N |
|---|---|---|---|
| Calculated | 7.21 | 74.74 | 13.07 |
| Found | 7.31 | 74.76 | 13.16 |

REFERENCE EXAMPLE 7

4-[3,4-Dihydro-2(1H)-quinazolinon-1-yl]-piperidine

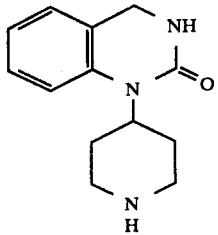

In this reference example, 16.0 g of 1-benzyl-4-[3,5-dihydro-2(1H)-quinazolinon-1-yl]-piperidine, 4.0 g of 10% Pd-C, 50 ml of 1 N hydrochloric acid, 150 ml of water and 300 ml of methanol are mixed and stirred at 40° C. Hydrogen gas is introduced to the mixture for 5 hours with stirring. Then, the Pd-C is removed by filtration and the filtrate is concentrated. The white crystalline residue is dissolved in 50 ml of water. The solution is adjusted to pH 10 with aqueous 5 N sodium hydroxide and extracted with chloroform. The extract is washed with water, dried and thereafter concentrated. Then, 50 ml of a mixture of ethyl acetate and n-hexane (1:1 by volume) is added to the residue. After trituration, the solid is separated by filtration, washed with the same mixed solvent to obtain 9.9 g of a crude product. The crude product is recrystallized from water-ethanol to obtain 5.1 g of the desired product.

Melting point: 153.0° to 155.0° C.

| Elementary analysis | H | C | N |
|---|---|---|---|
| Calculated | 7.41 | 67.51 | 18.17 |
| Found | 7.56 | 67.54 | 18.12 |

What is claimed is:

1. A piperidine derivative represented by the formula [I]:

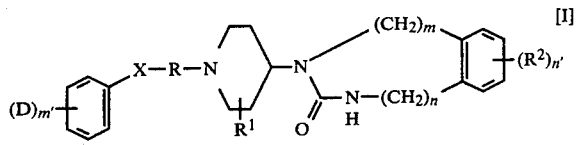

wherein m' is 0 or an integer of 1-5 representing the number of D groups; D is hydroxy, halogen, lower alkyl, lower alkoxy, lower alkenyloxy, lower alkynyloxy, lower alkylthio, carboxy, lower alkoxycarbonyl, nitro, amino, lower alkylamino, lower alkanoylamino, sulfamoyl, mono- or di-lower alkylaminosulfonyl, lower alkylsulfonyl, carbamoyl, cyano or trifluoromethyl, and when m' is 2 or more, each D is the same group or each D is a different group or two D groups may combine to form a lower alkylenedioxy; X is oxygen, sulfur, carbonyl, hydroxymethylene or methylene; R is straight-chain alkylene having 1-4 carbon atoms with or without lower alkyl substituent(s); $R^1$ is hydrogen or lower alkyl; m and n are 0 or 1, and m and n are different from each other; n' is 0 or an integer of 1-4 representing the number of $R^2$ groups substituted on the ring; and $R^2$ is hydroxy, lower alkoxy, halogen, trifluoromethyl, trifluoromethoxy, trifluoromethylthio, nitro or amino, and when n' is 2 or more, each $R^2$ is the same group or each $R^2$ is a different group or two $R^2$ groups may combine to form a lower alkylenedioxy and pharmacologically acceptable acid addition salts thereof.

2. A compound represented by the formula [I']:

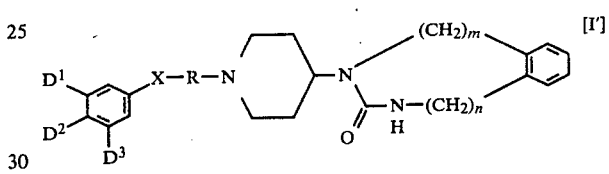

wherein $D^1$, $D^2$ and $D^3$ each represent the same groups or a different group, and each is hydrogen or hydroxy, halogen, lower alkyl, lower alkoxy, lower alkenyloxy, lower alkynyloxy, lower alkylthio, carboxy, lower alkoxycarbonyl, nitro, amino, lower alkylamino, lower alkanoylamino, sulfamoyl, mono- or di-lower alkylaminosulfonyl, lower alkylsulfonyl, carbamoyl, cyano or trifluoromethyl, or $D^1$ and $D^2$ or $D^2$ and $D^3$ may combine to form a lower alkylenedioxy; X is oxygen, sulfur, carbonyl, hydroxymethylene or methylene; R is straight-chain alkylene having 1-4 carbon atoms with or without lower alkyl substituent(s); $R^1$ is hydrogen or lower alkyl; m and n are 0 or 1, and m and n and different from each other; n' is 0 or an integer of 1-4 representing the number of $R^2$ groups substituted on the ring; and $R^2$ is hydroxy, lower alkoxy, halogen, trifluoromethyl, trifluoromethoxy, trifluoromethylthio, nitro or amino, and when n' is 2 or more, each $R^2$ is the same group or each $R^2$ is a different group or two $R^2$ groups may combine to form a lower alkylenedioxy and pharmacologically acceptable acid addition salts thereof.

3. A compound according to claim 2 wherein at least one of $D^1$, $D^2$ and $D^3$ is lower alkoxy or halogen, or $D^1$ and $D^2$ or $D^2$ and $D^3$ combine to form a lower alkylenedioxy.

4. A compound according to claim 2 wherein X is carbonyl or hydroxymethylene.

5. A compound according to claim 2 wherein R is methylene with or without lower alkyl substituent(s).

6. A pharmaceutical composition which comprises a pharmaceutically acceptable carrier, and an effective amount of a compound represented by the formula [I]:

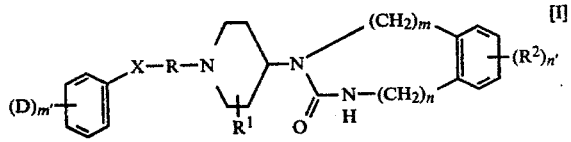

wherein m' is 0 or an integer of 1-5 representing the number of D groups substituted on the ring; D is hydroxy, halogen, lower alkyl, lower alkoxy, lower alkenyloxy, lower alkynyloxy, lower alkylthio, carboxy, lower alkoxycarbonyl, nitro, amino, lower alkylamino, lower alkanoylamino sulfamoyl, mono- or di-lower alkylaminosulfonyl, lower alkylsulfonyl, carbamoyl, cyano or trifluoromethyl, and when m' is 2 or more, each D is the same group or each D is a different group or two D groups may combine to form a lower alkylenedioxy; X is oxygen, sulfur, carbonyl, hydroxymethylene or methylene; R is straight-chain alkylene having 1-4 carbon atoms with or without lower alkyl substituent(s); $R^1$ is hydrogen or lower alkyl; m and n are 0 or 1, and m and n are different from each other; n' is 0 or an integer of 1-4 representing the number of $R^2$ groups substituted on the ring; and $R^2$ is hydroxy, lower alkoxy, halogen, trifluoromethyl, trifluoromethoxy, trifluoromethylthio, nitro or amino, and when n' is 2 or more, $R^2$ is the same or different or two $R^2$'s may combine to form lower alkylenedioxy or a pharmacologically acceptable acid addition salt thereof.

* * * * *